United States Patent
Dylewski et al.

(10) Patent No.: US 8,643,837 B2
(45) Date of Patent: Feb. 4, 2014

(54) METHODS AND MATERIALS FOR CALIBRATION OF A READER

(75) Inventors: Scott Dylewski, Sunnyvale, CA (US); Tong Xie, San Jose, CA (US); William Bilobran, Fremont, CA (US)

(73) Assignee: Alverix, Inc., San Jose, CA (US)

( * ) Notice: Subject to any disclaimer, the term of this patent is extended or adjusted under 35 U.S.C. 154(b) by 622 days.

(21) Appl. No.: 12/353,540

(22) Filed: Jan. 14, 2009

(65) Prior Publication Data

US 2010/0175455 A1    Jul. 15, 2010

(51) Int. Cl.
*G01J 1/10*    (2006.01)
*G01J 1/42*    (2006.01)
*G01N 21/00*   (2006.01)

(52) U.S. Cl.
USPC ............... 356/243.1; 356/228; 356/237.1

(58) Field of Classification Search
USPC ............... 356/237.1–241.6, 242.1–243.8, 356/426–431, 600–640
See application file for complete search history.

(56) References Cited

U.S. PATENT DOCUMENTS

| | | | | |
|---|---|---|---|---|
| 3,933,094 A * | 1/1976 | Murphy et al. | ............... | 283/88 |
| 5,320,808 A * | 6/1994 | Holen et al. | ............... | 422/64 |
| 5,387,503 A * | 2/1995 | Selmer et al. | ............... | 435/5 |
| 5,602,380 A * | 2/1997 | Bishay | ............... | 235/462.46 |
| 5,699,091 A * | 12/1997 | Bullock et al. | ............... | 347/19 |
| 5,851,488 A * | 12/1998 | Saul et al. | ............... | 422/67 |
| 6,937,323 B2 * | 8/2005 | Worthington et al. | ............... | 356/73 |
| 6,991,938 B1 * | 1/2006 | Cookson et al. | ............... | 436/164 |
| 7,347,973 B2 * | 3/2008 | Douglas et al. | ............... | 422/403 |
| 7,557,353 B2 * | 7/2009 | Black et al. | ............... | 250/370.07 |
| 7,888,125 B2 * | 2/2011 | Gibbons et al. | ............... | 436/8 |
| 7,939,342 B2 * | 5/2011 | Song et al. | ............... | 436/514 |
| 2003/0119202 A1 * | 6/2003 | Kaylor et al. | ............... | 436/514 |
| 2003/0119203 A1 * | 6/2003 | Wei et al. | ............... | 436/514 |
| 2007/0010022 A1 * | 1/2007 | Irvin | ............... | 436/80 |
| 2007/0081920 A1 * | 4/2007 | Murphy et al. | ............... | 422/58 |
| 2011/0073766 A1 * | 3/2011 | Johnson et al. | ............... | 250/370.07 |

\* cited by examiner

*Primary Examiner* — Gregory J Toatley
*Assistant Examiner* — Jarreas C. Underwood
(74) *Attorney, Agent, or Firm* — K&L Gates LLP

(57) ABSTRACT

The present disclosure relates generally to devices that may be used to calibrate a reader. Such devices may comprise an electrical memory chip, a calibration device comprising an optical check, and an interface that allows interaction with the reader.

46 Claims, No Drawings

METHODS AND MATERIALS FOR CALIBRATION OF A READER

BACKGROUND

Assay test kits currently are available for testing a wide variety of medical and environmental conditions or compounds, such as a hormone, a metabolite, a toxin, or a pathogen-derived antigen. Most commonly, these tests are used for medical diagnostics either for home testing, point of care testing, or laboratory use. For example, lateral flow tests are a form of immunoassay in which the test sample flows along a solid substrate via capillary action. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

A common problem with lateral flow assay test strips is that different test strips tend to produce slightly different results. Unfortunately, no two test strips will perform exactly alike (i.e. generate identical test result values) even if the test strips have the same amount of reagent embedded therein, and even if they are both exposed to the same amount of analyte. Such discrepancies in lateral flow assay test results may be explained by differences in the physical properties of individual test strips, the components used to read the assay test strip and also by differences in the fluid flow path along through different test strips. For example, the biological materials present on the assay test strip might degrade if the assay is stored in a hot or humid environment. In addition, the chemicals placed on the assay can be variable in their effectiveness simply due to the variations in the manufacturing process.

SUMMARY

The present disclosure provides methods and materials for calibrating a reader used for detecting the presence or absence of an analyte on an assay surface including, for example, a lateral flow assay test strip.

The present disclosure provides cartridges for calibration of a reader comprising: an electrical memory chip; a calibration device comprising an optical check; and an interface that allows interaction with the reader.

In an embodiment, the cartridge further comprises a power source. In an embodiment, the power source is a battery.

In an embodiment, the reader is an electronic reader.

In an embodiment, the optical check comprises a printed assay with no signal lines for optical or illumination checking. In an embodiment, the optical check comprises a printed assay with signal lines for optical or illumination checking. In an embodiment, the optical check comprises a printed assay with signal lines printed of known intensity for optical, illumination or algorithm checking.

In an embodiment, the optical check is a calibrated light source that verifies the optical properties of the detector in the reader. In an embodiment, the calibrated light source is a laser. In an embodiment, the calibrated light source is a LED.

In an embodiment, the optical check comprises wavelength specific detectors that measure the relative intensities of light from the reader.

In an embodiment, the electrical memory chip obtains information from the reader. In an embodiment, the electrical memory chip provides information to the reader. In an embodiment, the information is calibration or lot specific data. In an embodiment, the electrical memory chip loads new software into the reader.

In an embodiment, the cartridge interacts with the reader via wireless transmission. In an embodiment, the wireless transmission is RFID, WIFI, bluetooth or any combination thereof. In an embodiment, the cartridge interacts with the reader via optical transmission. In an embodiment, the optical transmission is IR.

In an embodiment, the electrical memory chip saves results obtained from the reader.

In an embodiment, the cartridge enables the reader if the optical check determines that the reader is calibrated. In an embodiment, the cartridge disables the reader if the optical check determines that the reader is not calibrated. In an embodiment, the cartridge disables the reader after a predetermined number of tests.

The present disclosure also provides cartridges for detecting information concerning storage or shipment of an assay comprising: a sensor that detects one or more environmental conditions that effect the assay; and a microcontroller for recording the one or more detected environmental conditions.

In an embodiment, the sensor is a temperature sensor. In an embodiment, the sensor is a humidity sensor.

In an embodiment, the sensor intermittently records the environmental condition. In an embodiment, the sensor continuously records the environmental condition.

In an embodiment, the cartridge may further comprise an indicator. In an embodiment, the indicator comprises a light. In an embodiment, the light illuminates when one or more detected environmental conditions exceeds a threshold.

In an embodiment, the cartridge further comprises an interface for providing the recorded environmental conditions to a reader.

In an embodiment, the reader is disabled when the recorded environmental conditions exceed a threshold.

In an embodiment, the cartridge further comprises a power source. In an embodiment, the power source is a battery.

The present disclosure also provides methods for providing calibration information to a reader used for measuring an analyte concentration from an assay, by providing the reader with a cartridge comprising an electrical memory chip; a calibration device comprising an optical check; and an interface that allows interaction with the reader; and allowing the calibration device to interact with the reader.

In an embodiment, the optical check obtains information from the reader. In an embodiment, the optical check provides information to the reader.

In an embodiment, the cartridge further comprises a power source. In an embodiment, the power source is a battery.

In an embodiment, the reader is an electronic reader.

In an embodiment, the assay is a lateral flow assay.

In an embodiment, the optical check is a calibrated light source that verifies the optical properties of the detector in the reader. In an embodiment, the calibrated light source is a laser. In an embodiment, the calibrated light source is a LED.

In an embodiment, the optical check comprises a printed assay with no signal lines for optical or illumination checking. In an embodiment, the optical check comprises a printed assay with signal lines for optical or illumination checking. In an embodiment, the optical check comprises a printed assay with signal lines printed of known intensity for optical, illumination or algorithm checking.

In an embodiment, the optical check comprises wavelength specific detectors that measure the relative intensities of light from the reader.

In an embodiment, the electrical memory chip obtains information from the reader. In an embodiment, the electrical memory chip provides information to the reader.

In an embodiment, the calibration device interacts with the reader via wireless transmission. In an embodiment, the wireless transmission is RFID, WIFI, bluetooth or any combination thereof. In an embodiment, the calibration device interacts with the reader via optical transmission. In an embodiment, the optical transmission is IR.

In an embodiment, the electrical memory chip saves results obtained from the reader. In an embodiment, the electrical memory chip provides information to the reader. In an embodiment, the information is calibration or lot specific data. In an embodiment, the electrical memory chip loads new software into the reader.

Additional features and advantages are described herein, and will be apparent from, the following Detailed Description.

DETAILED DESCRIPTION

The present disclosure provides methods and materials for calibrating a reader used to detect the presence or absence of an analyte on the surface of a lateral flow assay test strip. Two independent validations of a reader are often required to verify performance of the test device. For example, the electrical or opto-electronic reader may be validated to ensure that it is working correctly by placing an assay with a known good signal (or zero) in the reader and verifying that the reported result matches the known result. Any mismatch would indicate a reader that is not performing correctly. The assays may also be validated by running several assays with samples of known concentrations. If an analyte concentration of "5" is applied to the assay, then the system must report "5" as the result. Again, any mismatch would indicate that the assay or system is not performing correctly and requires calibration. The present disclosure provides devices and methods for calibration of a reader that may be used regardless upon whether or not the device has been found to be performing correctly.

The present disclosure provides devices (e.g., cartridges) for calibration of a reader, used to measure the presence or absence of an analyte on the surface of an assay test strip, that comprise an electrical memory chip, a calibration device comprising an optical check, and an interface that allows interaction with the reader. Such devices may be employed in methods to calibrate a reader. The device may save results obtained from the reader to a memory chip in the cartridge, load new software to the reader and/or load calibration or lot specific data from the cartridge. Optionally, the devices may further comprise a power source including, for example, a battery.

The present disclosure also provides cartridges for detecting information concerning storage or shipment of an assay comprising: a sensor that detects one or more environmental conditions that effect the assay; and a microcontroller for recording the one or more detected environmental conditions.

The cartridges of the present disclosure may interact with the reader via a direct wired contact or any other electrical contact known in the art. Alternatively, the cartridges of the present disclosure may interact with the reader via wireless transmission including, for example, RFID, WIFI, bluetooth or any combination thereof. Alternatively, the cartridge may interact with the reader via optical transmission including, for example, IR.

The cartridges of the present disclosure may be employed in methods for determining if a reader for measuring an analyte concentration from an assay is properly calibrated by: providing the reader with a device comprising calibration information, wherein the calibration information comprises a known concentration of analyte; obtaining a measurement from the reader with the calibration information; and comparing the measurement obtained from the reader with the known concentration of analyte from the calibration information, wherein the reader is properly calibrated where the reader obtains a measurement with the calibration information that is the same as the concentration of known analyte and wherein the reader is not properly calibrated where the reader obtains a measurement with the calibration information that is not the same as the concentration of known analyte.

The methods of the present disclosure are preferably used with an immunoassay device. One or more analytes bound to an antibody on the surface of the immunoassay device may be detected and subsequently quantitated.

Exemplary assays contemplated for use with the methods of the present disclosure include lateral flow assay test strips. Lateral flow assay test strips may comprise a membrane system that forms a single fluid flow pathway along the test strip. The membrane system may include one or more components that act as a solid support for immunoreactions. For example, porous, bibulous or absorbent materials may be placed on a strip such that they partially overlap, or a single material can be used, in order to conduct liquid along the strip. The membrane materials may be supported on a backing, such as a plastic backing. In a preferred embodiment, the test strip includes a glass fiber pad, a nitrocellulose strip and an absorbent cellulose paper strip supported on a plastic backing.

Antibodies that react with the target analyte and/or a detectable label system are immobilized on the solid support. The antibodies may be bound to the test strip by adsorption, ionic binding, van der Waals adsorption, electrostatic binding, or by covalent binding, by using a coupling agent, such as glutaraldehyde. For example, the antibodies may be applied to the conjugate pad and nitrocellulose strip using standard dispensing methods, such as a syringe pump, air brush, ceramic piston pump or drop-on-demand dispenser. In a preferred embodiment, a volumetric ceramic piston pump dispenser may be used to stripe antibodies that bind the analyte of interest, including a labeled antibody conjugate, onto a glass fiber conjugate pad and a nitrocellulose strip. The test strip may or may not be otherwise treated, for example, with sugar to facilitate mobility along the test strip or with water-soluble non-immune animal proteins, such as albumins, including bovine serum albumin (BSA), other animal proteins, water-soluble polyamino acids, or casein to block non-specific binding sites.

Any antibody, including polyclonal or monoclonal antibodies, or any fragment thereof, such as the Fab fragment, that binds the analyte of interest, is contemplated for use herein.

An antibody conjugate containing a detectable label may be used to bind the analyte of interest. The detectable label used in the antibody conjugate may be any physical or chemical label capable of being detected on a solid support using a reader, preferably a reflectance reader, and capable of being used to distinguish the reagents to be detected from other compounds and materials in the assay.

Suitable antibody labels are well known to those of skill in the art and include, but are not limited to, enzyme-substrate combinations that produce color upon reaction, colored particles, such as latex particles, colloidal metal or metal or carbon sol labels, fluorescent labels, and liposome or polymer sacs, which are detected due to aggregation of the label. In an embodiment, colloidal gold is used in the labeled antibody conjugate. The label may be derivatized for linking antibodies, such as by attaching functional groups, such as carboxyl groups to the surface of a particle to permit covalent attachment of antibodies. Antibodies may be conjugated to the label using well known coupling methods.

The assay test strip may be any conventional lateral flow assay test strip such as disclosed in EP 291194 or U.S. Pat. No. 6,352,862. The test strip may comprise a porous carrier containing a particulate labelled specific binding reagent and an unlabelled specific binding reagent. The light sources and corresponding photodetectors are preferably so aligned such that during use, light from the light source or sources falls upon the respective zones on the porous carrier and is reflected or transmitted to the respective photodetectors. The photodetectors generate a current roughly proportional to the amount of light falling upon it which is then fed through a resistor to generate a voltage. The amount of light reaching the photodetector depends upon the amount of coloured particulate label present and therefore the amount of analyte. Thus the amount of analyte present in the sample may be determined. This method of optically determining the analyte concentration is described more fully in EP 653625.

A sample may include, for example, anything which may contain an analyte of interest. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

A fluid sample (e.g., biological fluid) may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

Exemplary lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5939,331, 6,306,642.

A sample may include, for example, anything which may contain an analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). A liquid sample may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

An analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof (see, e.g., U.S. Pat. Nos. 4,366,241; 4,299,916; 4,275,149; and 4,806,311).

In an embodiment, a sample receiving zone on the surface of a lateral flow assay test strip accepts a fluid sample that may contain one or more analytes of interest. In an embodiment, the sample receiving zone is dipped into a fluid sample. A label zone is located downstream of the sample receiving zone, and contains one or more mobile label reagents that recognize, or are capable of binding the analytes of interest. Further, a test region may be disposed downstream from the label zone, and contains test and control zones. The test zone(s) generally contain means which permit the restraint of a particular analyte of interest in each test zone. Frequently, the means included in the test zone(s) comprise an immobilized capture reagent that binds to the analyte of interest. Generally the immobilized capture reagent specifically binds to the analyte of interest. Thus, as the fluid sample flows along the matrix, the analyte of interest will first bind with a mobilizable label reagent in the label zone, and then become restrained in the test zone.

In an embodiment, the sample receiving zone may be comprised of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be comprised of a material such as a nonwoven spunlaced acrylic fiber.

The sample receiving zone may be comprised of any material from which the fluid sample can pass to the label zone. Further, the absorbent application pad can be constructed to act as a filter for cellular components, hormones, particulate, and other certain substances that may occur in the fluid sample. Application pad materials suitable for use by the present invention also include those application pad materials disclosed in U.S. Pat. No. 5,075,078.

In a further embodiment, the sample receiving zone may be comprised of an additional sample application member (e.g., a wick). Thus, in one aspect, the sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. Moreover, the sample application member, if present, is positioned in fluid-flow contact with a sample application pad.

In an embodiment, the label zone material may be treated with labeled solution that includes material-blocking and label-stabilizing agents. Blocking agents include, for example, bovine serum albumin (BSA), methylated BSA, casein and nonfat dry milk. Stabilizing agents are readily available and well known in the art, and may be used, for example, to stabilize labeled reagents.

The label zone may contain a labeled reagent, often comprising one or more labeled reagents. In many of the presently contemplated embodiments, multiple types of labeled reagents are incorporated in the label zone such that they may permeate together with a fluid sample contacted with the device. These multiple types of labeled reagent can be analyte specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is not necessary due to the presence of test and control zones in the device, which allow for the accumulation of labeled reagent in designated zones.

The labeling zone may also include control-type reagents. These labeled control reagents often comprise detectible moieties that will not become restrained in the test zones and that are carried through to the test region and control zone(s) by fluid sample flow through the device. In a frequent embodiment, these detectible moieties are coupled to a member of a specific binding pair to form a control conjugate which can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced.

The test region may include a control zone for verification that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest. In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form).

In an embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectible signal (e.g., be of the same color) or provide distinguishable detectible signals (e.g., have different colored labels or other detection systems) upon accumulation in the control zone(s).

In an embodiment, the labeled control reagent comprises a detectible moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

The use of a control zone is helpful in that appearance of a signal in the control zone indicates the time at which the test result can be read, even for a negative result. Thus, when the expected signal appears in the control line, the presence or absence of a signal in a test zone can be noted.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectible signal. Devices may incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices may optionally further comprise an absorbent zone that acts to absorb excess sample after the sample migrates through the test region. The absorbent zone, when present lies in fluid flow contact with the test region. This fluid flow contact can comprise an overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones.

The test strip optionally may be contained within a housing for insertion into the reflectance reader. The housing may be made of plastic or other inert material that does not interfere with the assay procedure.

The lateral flow assay test strip may be suited for use with a reading device that comprises one or more of the following: a central processing unit (CPU) or microcontroller; one or more LED's; one or more photodiodes; a power source; and associated electrical circuitry. The power source may comprise a battery or any other suitable power source (e.g. a photovoltaic cell). The CPU will typically be programmed so as to determine whether the calculated rate and/or extent of progress of the liquid sample is within predetermined limits.

Conveniently the assay result reading device will comprise some manner of indicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether the calculated rate and/or extent of progress of the liquid sample is within the predetermined acceptable limits, and thus whether or not the result of the particular assay should be disregarded. If the reading device determines that a particular assay result should be disregarded it may prompt the user to repeat the assay.

Any device which is compatible for use with an assay test strip, preferably a reflectance reader, for determining the assay result is contemplated for use herein. Such test strip devices as are known to those of skill in the art (see, e.g., U.S. Pat. Nos. 5,658,801, 5,656,502, 5,591,645, 5,500,375, 5,252,459, 5,132,097). Reflectance and other readers, including densitometers and transmittance readers, are known to those of skill in the art (see, e.g., U.S. Pat. Nos. 5,598,007, 5,132,097, 5,094,955, 4,267,261, 5,118,183, 5,661,563, 4,647,544, 4,197,088, 4,666,309, 5,457,313, 3,905,767, 5,198,369, 4,400,353).

It should be understood by those skilled in the art that various modifications, combinations, sub-combinations and alterations may occur depending on design requirements and other factors insofar as they are within the scope of the appended claims or the equivalents thereof.

The invention claimed is:

1. A cartridge for calibration of a reader, said cartridge comprising:
    an electrical memory chip;
    a calibration device comprising an optical check for calibration of the reader, the optical check configured for determining whether the reader is calibrated to measure an analyte; and
    an interface that allows interaction with the reader.

2. The cartridge of claim 1, wherein the cartridge further comprises a power source.

3. The cartridge of claim 2, wherein the power source is a battery.

4. The cartridge of claim 1, wherein the reader is an electronic reader.

5. The cartridge of claim 1, wherein the optical check comprises a printed assay with no signal lines for optical or illumination checking.

6. The cartridge of claim 1, wherein the optical check comprises a printed assay with signal lines for optical or illumination checking.

7. The cartridge of claim 1, wherein the optical check comprises a printed assay with signal lines printed of known intensity for optical, illumination or algorithm checking.

8. The cartridge of claim 1, wherein the optical check is a calibrated light source that verifies the optical properties of a detector in the reader.

9. The cartridge of claim 8, wherein the calibrated light source is a laser.

10. The cartridge of claim 8, wherein the calibrated light source is a LED.

11. The cartridge of claim 1, wherein the optical check comprises wavelength specific detectors that measure the relative intensities of light from the reader.

12. The cartridge of claim 1, wherein the electrical memory chip obtains information from the reader.

13. The cartridge of claim 1, wherein the electrical memory chip provides information to the reader.

14. The cartridge of claim 13, wherein the information is calibration or lot specific data.

15. The cartridge of claim 13, wherein the electrical memory chip loads new software into the reader.

16. The cartridge of claim 1, wherein the cartridge interacts with the reader via a direct electrical contact or wireless transmission.

17. The cartridge of claim 16, wherein the wireless transmission is RFID, WIFI, bluetooth or any combination thereof.

18. The cartridge of claim 1, wherein the cartridge interacts with the reader via optical transmission.

19. The cartridge of claim 18, wherein the optical transmission is IR.

20. The cartridge of claim 1, wherein the electrical memory chip saves results obtained from the reader.

21. The cartridge of claim 1, wherein the cartridge enables the reader if the optical check determines that the reader is calibrated.

22. The cartridge of claim 1, wherein the cartridge disables the reader if the optical check determines that the reader is not calibrated.

23. The cartridge of claim 1, wherein the cartridge disables the reader after a predetermined number of tests.

24. A method for providing calibration information to a reader used for measuring an analyte from an assay, said method comprising:
   providing the reader with a cartridge comprising
      an electrical memory chip;
      a calibration device comprising an optical check for calibration of the reader, the optical check configured for determining whether the reader is calibrated to measure an analyte; and
      an interface that allows interaction with the reader; and
   allowing the calibration device to interact with the reader.

25. The method of claim 24, wherein the optical check obtains information from the reader.

26. The method of claim 24, wherein the optical check provides information to the reader.

27. The method of claim 24, wherein the cartridge further comprises a power source.

28. The method of claim 27, wherein the power source is a battery.

29. The method of claim 24, wherein the reader is an electronic reader.

30. The method of claim 24, wherein the assay is a lateral flow assay.

31. The method of claim 24, wherein the optical check is a calibrated light source that verifies the optical properties of a detector in the reader.

32. The method of claim 31, wherein the calibrated light source is a laser.

33. The method of claim 31, wherein the calibrated light source is a LED.

34. The method of claim 24, wherein the optical check comprises a printed assay with no signal lines for optical or illumination checking.

35. The method of claim 24, wherein the optical check comprises a printed assay with signal lines for optical or illumination checking.

36. The method of claim 24, wherein the optical check comprises a printed assay with signal lines printed of known intensity for optical, illumination or algorithm checking.

37. The method of claim 24, wherein the optical check comprises wavelength specific detectors that measure the relative intensities of light from the reader.

38. The method of claim 24, wherein the electrical memory chip obtains information from the reader.

39. The method of claim 24, wherein the electrical memory chip provides information to the reader.

40. The method of claim 24, wherein the calibration device interacts with the reader via a direct electrical contact or wireless transmission.

41. The method of claim 40, wherein the wireless transmission is RFID, WIFI, bluetooth or any combination thereof.

42. The method of claim 24, wherein the calibration device interacts with the reader via optical transmission.

43. The method of claim 42, wherein the optical transmission is IR.

44. The method of claim 24, wherein the electrical memory chip saves results obtained from the reader.

45. The cartridge of claim 39, wherein the information is calibration or lot specific data.

46. The cartridge of claim 24, wherein the electrical memory chip loads new software into the reader.

* * * * *